US012613229B2

(12) United States Patent
Amin et al.

(10) Patent No.: US 12,613,229 B2
(45) Date of Patent: Apr. 28, 2026

(54) MOBILE COMMUNICATIONS DEVICE WITH ELECTRONIC NOSE

(71) Applicants: Alexander Himanshu Amin, Solon, OH (US); Himanshu Subhash Amin, Solon, OH (US)

(72) Inventors: Alexander Himanshu Amin, Solon, OH (US); Himanshu Subhash Amin, Solon, OH (US)

( * ) Notice: Subject to any disclaimer, the term of this patent is extended or adjusted under 35 U.S.C. 154(b) by 0 days.

(21) Appl. No.: 18/453,799

(22) Filed: Aug. 22, 2023

(65) Prior Publication Data

US 2023/0393110 A1     Dec. 7, 2023

Related U.S. Application Data

(63) Continuation of application No. 17/539,589, filed on Dec. 1, 2021, now Pat. No. 11,782,037, which is a continuation of application No. 16/875,453, filed on May 15, 2020, now Pat. No. 11,215,595, which is a continuation of application No. 16/290,330, filed on Mar. 1, 2019, now Pat. No. 10,697,948, which is a continuation of application No. 15/460,124, filed on Mar. 15, 2017, now Pat. No. 10,254,260, which is a
(Continued)

(51) Int. Cl.
| | |
|---|---|
| *G01N 33/00* | (2006.01) |
| *G06F 16/951* | (2019.01) |
| *H04W 4/02* | (2018.01) |
| *H04W 4/029* | (2018.01) |
| *H04W 88/02* | (2009.01) |

(52) U.S. Cl.
CPC ....... *G01N 33/0031* (2013.01); *G06F 16/951* (2019.01); *H04W 4/02* (2013.01); *H04W 4/029* (2018.02); *H04W 88/02* (2013.01)

(58) Field of Classification Search
CPC ........... G01N 33/0031; G01N 30/8651; G06F 16/951; H04W 4/02; H04W 4/029; H04W 88/02
See application file for complete search history.

(56) References Cited

U.S. PATENT DOCUMENTS

| | | | |
|---|---|---|---|
| 5,523,569 | A | 6/1996 | Hornfeld et al. |
| 6,532,801 | B1 | 3/2003 | Shan et al. |
| 6,672,129 | B1 | 1/2004 | Frederickson et al. |

(Continued)

OTHER PUBLICATIONS

Final Office Action received for U.S. Appl. No. 17/092,849, dated Jul. 22, 2024, 30 pages.

(Continued)

*Primary Examiner* — Manuel L Barbee
(74) *Attorney, Agent, or Firm* — Amin, Turocy & Watson, LLP

(57) ABSTRACT
Systems and methods for a mobile electronic system that gathers and analyzes odors, airborne chemicals and/or compounds. The system includes a sample delivery component that can gather airborne substances and/or gaseous substances. A detection component can detect the presences of chemicals, substances, and/or visual gases in a sample. Analyzed samples can be compared with known substance and/or odor analysis. In addition, the source of the sample can be determined. Accordingly, odor, gas, and/or airborne substance identification can be accomplished.

20 Claims, 12 Drawing Sheets

Related U.S. Application Data continuation of application No. 13/839,206, filed on Mar. 15, 2013, now Pat. No. 9,645,127.

(60) Provisional application No. 61/643,781, filed on May 7, 2012.

(56) References Cited

U.S. PATENT DOCUMENTS

| | | | |
|---|---|---|---|
| 7,827,189 | B2 | 11/2010 | Hayama |
| 8,038,948 | B1 | 10/2011 | Laughlin |
| 8,190,443 | B1 | 5/2012 | Ouzounian |
| 10,254,260 | B2 | 4/2019 | Amin et al. |
| 10,697,948 | B2 | 6/2020 | Amin et al. |
| 2001/0045953 | A1 | 11/2001 | Staples |
| 2002/0000115 | A1 | 1/2002 | Nakano et al. |
| 2003/0086091 | A1 | 5/2003 | Hinnrichs et al. |
| 2004/0101851 | A1 | 5/2004 | White et al. |
| 2004/0169071 | A1 | 9/2004 | Burgan et al. |
| 2005/0168749 | A1 | 8/2005 | Ye et al. |
| 2006/0191319 | A1* | 8/2006 | Kurup ............... G01N 33/0034 73/23.34 |
| 2008/0040344 | A1 | 2/2008 | Hayama |
| 2008/0188172 | A1 | 8/2008 | Hollemans et al. |
| 2008/0262743 | A1 | 10/2008 | Lewis et al. |
| 2009/0125641 | A1 | 5/2009 | Garbow et al. |
| 2009/0147104 | A1 | 6/2009 | Wang |
| 2009/0159798 | A1 | 6/2009 | Weida et al. |
| 2010/0131206 | A1* | 5/2010 | Angell ................... G06Q 30/02 702/23 |
| 2011/0172931 | A1 | 7/2011 | Murthy |
| 2011/0184740 | A1 | 7/2011 | Gruenstein et al. |
| 2012/0024042 | A1 | 2/2012 | Vass et al. |
| 2012/0111314 | A1 | 5/2012 | Corleoni |
| 2013/0191250 | A1 | 7/2013 | Bradley et al. |
| 2014/0156412 | A1 | 6/2014 | Tse |
| 2017/0070845 | A1 | 3/2017 | Edwards et al. |

OTHER PUBLICATIONS

Non-Final Office Action received for U.S. Appl. No. 16/736,083, dated Jun. 5, 2024, 32 pages.
Non-Final Office Action received for U.S. Appl. No. 14/219,914 dated Jul. 17, 2014, 47 pages.
Notice of Allowance received for U.S. Appl. No. 14/219,914 dated Nov. 6, 2014, 34 pages.
Non-Final Office Action received for U.S. Appl. No. 13/839,206 dated Jan. 6, 2016, 28 pages.
Non-Final Office Action received for U.S. Appl. No. 14/560,779 dated Feb. 26, 2016, 46 pages.
Final Office Action received for U.S. Appl. No. 13/839,206 dated Sep. 7, 2016, 25 pages.
Non-Final Office Action received for U.S. Appl. No. 14/560,779 dated Aug. 29, 2016, 37 pages.
Notice of Allowance received for U.S. Appl. No. 13/839,206 dated Mar. 27, 2017, 19 pages.
Non-Final Office Action received for U.S. Appl. No. 14/560,779 dated May 22, 2017, 37 pages.
Final Office Action received for U.S. Appl. No. 14/560,779 dated Dec. 29, 2017, 44 pages.
Non-Final Office Action received for U.S. Appl. No. 15/460,124 dated Apr. 11, 2018, 29 pages.
Non-Final Office Action received for U.S. Appl. No. 14/560,779 dated Jul. 27, 2018, 50 pages.
Ishida et al., "Mobile Robot Navigation Using Vision and Olfaction to Search for a Gadodor Source", IEEE, 2004, 313-318.
Final Office Action received for U.S. Appl. No. 15/460,124 dated Sep. 18, 2018, 20 pages.
Final Office Action received for U.S. Appl. No. 14/560,779 dated Nov. 29, 2018, 23 pages.
Non-Final Office Action received for U.S. Appl. No. 15/333,559 dated Jan. 11, 2019, 59 pages.
Non-Final Office Action received for U.S. Appl. No. 14/560,779 dated Jun. 21, 2019, 26 pages.
Non-Final Office Action received for U.S. Appl. No. 15/333,559 dated Nov. 1, 2019, 40 pages.
Non-Final Office Action received for U.S. Appl. No. 16/290,330 dated Oct. 4, 2019, 23 pages.
Non-Final Office Action received for U.S. Appl. No. 16/290,330 dated Dec. 12, 2019, 11 pages.
Non-Final Office Action received for U.S. Appl. No. 15/333,559 dated Jun. 12, 2020, 13 pages.
Non-Final Office Action received for U.S. Appl. No. 16/875,453 dated Apr. 1, 2021, 27 pages.
Non-Final Office Action received for U.S. Appl. No. 16/736,083 dated Jan. 21, 2022, 58 pages.
Final Office Action received for U.S. Appl. No. 16/736,083 dated Jul. 20, 2022, 23 pages.
Non-Final Office Action received for U.S. Appl. No. 17/092,849 dated Jul. 20, 2022, 63 pages.
Non-Final Office Action received for U.S. Appl. No. 16/736,083 dated Nov. 8, 2022, 28 pages.
Final Office Action received for U.S. Appl. No. 17/092,849 dated Dec. 8, 2022, 32 pages.
Non-Final Office Action received for U.S. Appl. No. 17/539,589 dated Mar. 7, 2023, 44 pages.
Final Office Action received for U.S. Appl. No. 16/736,083 dated Apr. 13, 2023, 31 pages.
Non-Final Office Action received for U.S. Appl. No. 17/092,849 dated Mar. 30, 2023, 35 pages.
Notice of Allowance received for U.S. Appl. No. 17/539,589 dated Jun. 7, 2023, 20 pages.
Final Office Action received for U.S. Appl. No. 17/092,849 dated Jul. 26, 2023, 31 pages.
Non-Final Office Action received for U.S. Appl. No. 16/736,083 dated Sep. 21, 2023, 32 pages.
Non-Final Office Action received for U.S. Appl. No. 17/092,849, dated Jan. 31, 2024, 33 pages.
Final Office Action received for U.S. Appl. No. 16/736,083, dated Jan. 17, 2024, 29 pages.
Final Office Action received for U.S. Appl. No. 16/736,083, dated Oct. 17, 2024, 22 pages.
Notice of Allowance received for U.S. Appl. No. 16/736,083 dated Jan. 23, 2025, 24 pages.
Non-Final Office Action received for U.S. Appl. No. 17/092,849 dated Dec. 31, 2024, 37 pages.
Final Office Action received for U.S. Appl. No. 17/092,849 dated Mar. 11, 2025, 36 pages.
Notice of Allowance received for U.S. Appl. No. 17/092,849 dated Jul. 29, 2025, 16 pages.

* cited by examiner

700

<u>702</u>

RECEIVE SAMPLE

<u>704</u>

ANALYZE HEADSPACE

<u>706</u>

COMPARE ANALYZED HEADPACE

<u>708</u>

DETERMINE SOURCE

<u>710</u>

OUTPUT RESULT

800

802

RECEIVE SAMPLE

804

RECEIVE INPUT

806

ANALYZE HEADSPACE

808

COMPARE ANALYZED HEADSPACE

810

DETERMINE SOURCE

812

900

902

ANALYZE HEADSPACE

904

COMPARE ANALYZED HEADSPACE WITH
SERVER ENTRIES

906

DETERMINE SOURCE

MOBILE COMMUNICATIONS DEVICE WITH ELECTRONIC NOSE

CROSS REFERENCE TO RELATED APPLICATIONS

This application is a continuation of U.S. Non-Provisional application Ser. No. 17/539,589 filed Dec. 1, 2021 and entitled "MOBILE COMMUNICATIONS DEVICE WITH ELECTRONIC NOSE," which is a continuation of U.S. Non-provisional application Ser. No. 16/875,453 filed May 15, 2020 (now U.S. Pat. No. 11,215,595) and entitled "MOBILE COMMUNICATIONS DEVICE WITH ELEC-TRONIC NOSE", which is a continuation of U.S. Non-provisional application Ser. No. 16/290,330 filed Mar. 1, 2019 (now U.S. Pat. No. 10,697,948) and entitled "MOBILE COMMUNICATIONS DEVICE WITH ELECTRONIC NOSE", which is a continuation of U.S. Non-provisional application Ser. No. 15/460,124 filed Mar. 15, 2017 (now U.S. Pat. No. 10,254,260) and entitled "MOBILE COM-MUNICATIONS DEVICE WITH ELECTRONIC NOSE", which is a continuation of U.S. Non-provisional application Ser. No. 13/839,206 filed Mar. 15, 2013 (now U.S. Pat. No. 9,645,127) and entitled "ELECTRONIC NOSE SYSTEM AND METHOD", which claims priority to U.S. Provisional Application Ser. No. 61/643,781 filed May 7, 2012 and entitled "ELECTRONIC NOSE SYSTEM AND METHOD"; the entireties of each application are incorporated herein by reference.

TECHNICAL FIELD

This disclosure relates to detection of chemical compounds, gases, and odor. More particularly to methods and systems for detection of chemicals or gases in air samples through a portable handheld device.

BACKGROUND

The proliferation, advancement, and affordability of electronic computing devices such as smart phones, laptop computers, personal computers, digital cameras, tablets, personal digital assistants (PDAs) and other electronic devices has made powerful electronic devices more available to the general public than ever before. Advancements in detection devices capable of odor detection, chemical detection and gas detection have made some detection devices common place in homes. For example, a sensor that can indicate presence of a chemical, gas or substance of interest can be useful to identify an unacceptable level of a toxic or explosive gas. There is an unmet need by the state of the art for convenient, rapid and reliable identification or detection of chemicals, gases, compounds, substances and the like.

SUMMARY

The following presents a simplified summary of the specification in order to provide a basic understanding of some aspects of the specification. This summary is not an extensive overview of the specification. It is intended to neither identify key or critical elements of the specification nor delineate the scope of any particular implementations of the specification, or any scope of the claims. Its purpose is to present some concepts of the specification in a simplified form as a prelude to the more detailed description that is presented in this disclosure.

Systems and methods disclosed herein relate to detection of odors, chemicals and gasses via handheld electronic devices (e.g., mobile phone). A sample delivery component is coupled to an electronic processor. The sample delivery component collects a headspace of a sample. The headspace is a portion of the sample that is to be analyzed. The sample delivery component can passively and/or actively collect the headspace of a sample by drawing air, for example.

A detection component is coupled to the electronic processor and sample delivery component. The detection component can analyze the headspace. The headspace analysis can determine presence and ratio of chemical, physical, and/or visual substances the make-up the headspace. Aspects of the detection component and the electronic processor can be coupled to a computer readable memory. The memory can store known analyzed samples of chemicals, gases, and/or odors, e.g., in the form of digital signatures, hash values, or any suitable use of identifying indicia or representation. The detection component can compare the analyzed headspace to known analyzed samples in the memory to determine the source of the headspace (e.g., flower, foodstuff, alcohol, perfume, etc.) and/or associate the analyzed headspace with a known source. In another example, when an analyzed headspace is determined to be a new combination of odors, gases, and/or chemicals, then the new combination of odors, gases, and/or chemicals can be stored in the memory.

In another embodiment, the detection component can determine if the headspace is a visual gas such as smoke without comparing the headspace to samples stored in memory. In this embodiment, the detection component can visually analyze the headspace.

In another embodiment, an image detection component (e.g., camera) can capture an image of a source of the headspace. The detection component can receive the captured image and determine the source of the headspace via analysis of the captured image, the analyzed headspace, or a combination thereof.

A display component displays can display a result of the analyzed headspace. The result can be a known source (e.g., type of flower, type of perfume, etc.). The result can comprise text and/or image. In one example, a result can be saved in memory and associated with as a new odor, gas, or chemical source.

The following description and the drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, and advantages of the present invention will be apparent upon consideration of the following detailed description, taken in conjunction with the accompanying drawings, in which like reference characters refer to like parts throughout, and in which.

DETAILED DESCRIPTION

Figure 1:
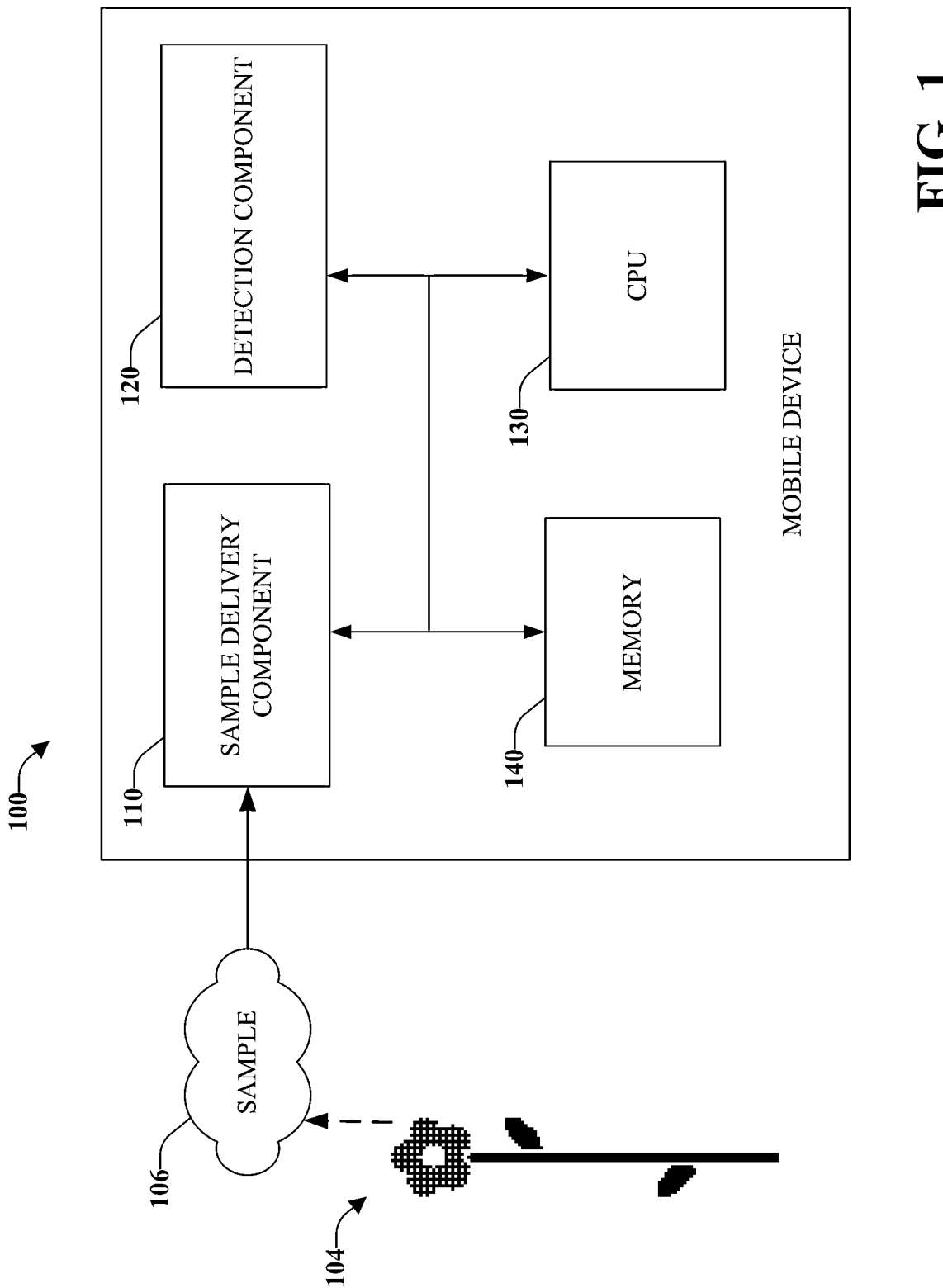
FIG. 1 illustrates a high-level functional block diagram of an example mobile electronic nose device.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that certain aspects of disclosure may be practiced without these specific details, or with other methods, components, materials, etc. In other instances, well-known structures and devices are shown in block diagram form to facilitate describing this disclosure.

Systems and methods disclosed herein relate to detection of odors, chemicals and/or gasses via handheld electronic devices. In one implementation, a mobile device receives, determines and identifies a source of a headspace of a sample. The mobile device is an electronic computing device such as for example a smartphone, tablet, PDA, laptop, cookware with circuitry, cooking utensils with circuitry, and the like.

In one embodiment, the mobile device passively receives a sample such as chemicals, gas, or odors. The sample can be received through openings in a body of the mobile device. In another embodiment, a mobile device actively draws in the sample via a sample delivery component. The sample delivery component can include an intake device such as a fan (e.g., bladed fan, air foil fan and the like), or a manually powered pump, for example. The intake device can pull air from outside the mobile device creating a positive pressure inside the device relative to the outside pressure. This causes air to pass through the device.

A detection component, coupled to a memory and a CPU, of the mobile device can receive a sample of the air. The detection component can analyze a headspace (portion) of the sample. The detection component can detect presence and amount of chemicals in the headspace. In one implementation, the detection component can include a sensory array. The sensory array can react to various chemicals within the headspace. The reaction can cause a change in physical or electrical properties of the sensory array. In one example, absorption of the chemicals in the headspace causes physical alterations of the various sensors in the sensory array. Each sensory array can react differently to the various chemicals. A CPU can transform the reactions of the sensory array into a digital signal. The digital signal can be computed based on a statistical model. For example, in one non-limiting embodiment, an organic ultra-thin transistor chemical sensor having a channel that consists of one or a few monolayers can be employed. The organic thin film transistor chemical sensors can have nearly monolayer thin film channels that act as highly-sensitive detectors of trace levels of organic vapors and can perform quantitative vapor analysis. The organic ultra-thin film can be permeable to a chemical analyte of interest.

A memory can store digital signals associated with sources (e.g., a rose, a foodstuff, burning foodstuff, etc.). In one embodiment, the detection component compares the digital signal associated with the headspace to the stored digital signals within the memory. The detection component can then find the best match and determine the source of the headspace. In another embodiment, the mobile device can compare the digital signal associated with the headspace to a memory of a server, such as a server connected via cellular communication networks, intranet, internet or similar communication networks known in the art.

In another example, the detection component can determine that a best matched sample is not in memory. In this case, a new source is associated with the digital signal associated to the headspace. An input component can receive information about the source. The memory can store the associated source with the digital signal.

In another example, the mobile device can receive a plurality of headspaces associated with the same sample via the sample delivery component. The detection component can normalize the plurality of headspaces into a normalized headspace. The normalized headspace can be analyzed as above.

In another embodiment, input component can receive information about a source of a sample. In one example, the information can include text, location information (via global positioning satellites, user input, wireless access points, wired access points, etc.), audio information, and/or image information. The detection component can analyze the received information and the headspace to determine the source of the sample. In one implementation, the information received by the input component can narrow the possible sources to be associated with the headspace to be of a certain genus or type. For example, a voice capturing device can receive audio and determine that the audio contains a phrase such as "identify this flower". Thus, the detection component narrows the possible sources to flowers.

In another implementation, the detection component can detect if a food substance is expired, not expired, or the quality. For example, the detection component can determine if milk or wine has gone bad by comparing an analyzed headspace's associated digital signal to a known digital signal. In one aspect, input information can be received as text or audio information such as "is this wine spoiled?" and the detection component can reduce the amount of digital signals to compare to an analyzed headspace's digital signal.

In one example, the input component can include an image capturing device (e.g., a camera) can capture an image of a source associated with a sample and send the image to the detection component. The detection component analyzed the image of the source and the headspace of the sample associated with the source. The determination of the source can be enhanced and/or speed-up through the dual analysis of the captured image and the headspace. As one example, the captured image can narrow the possible sources of the headspace. For example, a sample of the fragrance of a flower can be received and an image of the flower can be captured. The detection component can determine the headspace is associated with a flower via analysis of the image of the flower.

Some non-limiting examples of types of sensors or detectors that can be employed in connection with identification of samples include: a calorimeter, a conductivity sensor, an enzymatic sensor, a biosensor, a chemical sensor, an Enzyme-Linked Assay sensor (e.g., an Enzyme-Linked Immunosorbent Assay (ELISA) sensor), an infrared (IR) spectroscopy sensor, a Nuclear Magnetic Resonance (NMR) sensor, an optical sensor, a permittivity sensor, a gas sensor, a Radio Frequency (RF) sensor, an electronic tongue sensor, a multi-frequency RF sensor, a cantilever sensor, an acoustic wave sensor, a piezoelectric sensor, a responsive polymer-based sensor, a quartz microbalance sensor, a metal oxide sensor, an X-ray Fluorescence (XRF) sensor, a nucleic acid-based sensor (e.g., a DNA-, RNA-, or aptamer-based sensor), or a regenerable sensor.

Furthermore, it is to be appreciated that multiple modalities can be employed in connection with converging on identification of a sample. For example, image or video capture components of a mobile device can be employed to identify item(s) of interest to be analyzed, audio analysis, voice analysis, text, can be employed in connection with determining identification goals of a user as well as determining properties of items that are analyzed. A user can take an image of an item (e.g., a snack) and utter is this allergen safe? The image can be analyzed (e.g., using pattern recognition) to identify that it is a cookie as well as likely type of cookie (e.g., peanut butter). Based on the utterance, the system determines that the user is interested in ensuring that the cookie does not include items that may cause an allergic reaction (e.g., nut allergy). The electronic nose can be employed to detect presence of nuts in the cookie or any other potential allergen that might affect the user. Accordingly, the combination of pattern, voice and smell detection can provide a higher confidence level regarding item and goal determination as compared to using just one sensing modality.

Moreover, geographic location, time of day, season, etc. can also be employed in connection with facilitating identification. For example, a global positioning system (GPS) component of the mobile device can provide geographic location, and such information coupled with temporal or season information can facilitate factoring likelihood of gases, chemicals, substances, compounds, allergens or the like that have a high or low probability of presence at such location and time. If the mobile device is located in Ohio during the month of May, likelihood of certain allergens (e.g., tree and grass pollens) can be factored into a determination of presence of certain items of interest. Likewise, if the mobile device is located in the Arctic Circle, and the device is located outside the likelihood of a live plant or animal being a source of an item is relatively low. In yet another example, identification of location within a particular restaurant can also be employed to facilitate item identification. If the restaurant is an Indian restaurant as compared to a steak house, the presence of certain exotic spices (e.g., turmeric, saffron, garam masala, cumin, coriander, etc.) is likely to be higher than in the steak house.

Embodiments disclosed herein can leverage multiple modalities (e.g., image or pattern recognition, location based services, web-based search tools, electronic noses, chemical sensors, audio recognition, time, date, season, location, etc.) to facilitate converging on user item identification goals as well as item identification.

Sensors can be self-cleaning (e.g., vibration, light, chemical or gas washes, etc.) as well as disposable.

In the smelling process of the human olfactory system, the initial step is to bind specific odorants to the olfactory receptor protein which triggers signal transduction in a cell. Olfactory receptors expressed in the cell membranes of olfactory receptor neurons are responsible for the detection of odorant molecules. That is, when the odorants bind to the olfactory receptors as described above, the receptors are activated. The activated olfactory receptors are the initial player in a signal transduction cascade which ultimately produces a nerve impulse which is transmitted to the brain. These olfactory receptors are members of the class A rhodopsin-like family of G protein-coupled receptors (GPCRs). In accordance with an embodiment, an olfactory receptor-functionalized transistor is provided, that is useful for a bioelectronic nose which can detect and analyze specific odorants with high selectivity, by functionalizing a nanostructure transistor with an olfactory receptor (e.g., a lipid membrane having an olfactory receptor protein is formed to cover surfaces of a source electrode, a drain electrode, and a nanostructure).

The olfactory receptor protein belongs to a family of G-protein coupled receptors and may exist over the surface of, the interior of, or the surface and interior of a lipid double membrane. An olfactory receptor membrane generally includes an ionizable cysteine residue and exists in a conformational equilibrium between biophysically activated and non-activated states. The activated and non-activated states of the olfactory receptor molecule are associated with a negatively-charged base form and a neutral acid form of cysteine, respectively. When specific odorants bind to olfactory receptor molecules, equilibrium of receptor molecules moves to an activated receptor form having negative charges. The negative charges of the olfactory receptor molecules which were changed into an activated state modulate contact resistance between metal electrode and nanostructure, leading to reduction in conductance. In accordance with an embodiment, odorant molecules can be detected highly selectively based on electrostatic perturbation of a nanostructure junction generated from a conformational change by binding odorants to olfactory receptor molecules. Thus, highly-specific detection of odorants with femtomolar sensitivity can be achieved in real time, and various and novel applications such as a highly selective artificial nose application can be achieved. In one embodiment, the nanostructure may be at least one form selected from the group consisting of nanotube, nanowire, nanorod, nanoribbon, nanofilm, and nanoball. For example, semiconductor nanowires such as silicon nanowires, and carbon nanotubes may be used, and a single-walled carbon nanotube can provide desirable high biocompatibility and device characteristics.

In another embodiment, a random network of single-walled carbon nanotubes (SWCNTs) coated with non-polar small organic molecules in conjunction with learning and pattern recognition algorithms (e.g., artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor) can be employed. For example, detection of volatile compounds as biomarkers for diagnosis of medical conditions can be performed using olfactometry systems that perform odor detection through use of an array of cross-reactive sensors in conjunction with pattern recognition algorithms. Each sensor can be widely responsive to a variety of odorants. Each analyte can produce a distinct signature from an array of broadly cross-reactive sensors. This configuration allows to considerably widen the variety of compounds to which a given matrix is sensitive, to increase degree of component identification and, in specific cases, to perform an analysis of individual components in complex multi-component mixtures. Pattern recognition algorithms can then be applied to the entire set of signals, obtained concurrently from a set (e.g., one or more) of sensors in the array, in order to glean information on identity, properties and concentration of vapor exposed to the sensor array.

Referring now to FIG. 1, there is illustrated a non-limiting exemplary implementation of a mobile device 110 in accordance with various aspects of this disclosure. The mobile device 110 includes a sample delivery component 111, a detection component 120, a computer processing unit (CPU) 130, and a memory 140. The mobile device 110 provides for gathering samples, and detecting and identifying source of a sample. The mobile device 110 receives sample 116 associated with a source 114. Sample 116 can be an odor, chemical, and/or airborne fragrance given off by source 114. In one aspect, CPU 130 is capable of executing various components and/or portions of components stored in a computer readable memory 140.

The sample delivery component 111 can receive the sample 116. In one implementation, the sample delivery component 111 passively receives the sample 116 as the sample 116 diffuses. In another implementation, the sample delivery component 111 actively gathers the sample 116. For example, sample delivery component 111 can comprise an intake component that draws air into the mobile device 110 or a portion of the mobile device by creating a negative air pressure in the mobile device 110 or the portion of the mobile device relative to an external air pressure.

The sample delivery component 111 is in fluid communication with the detection component 120. Detection component 120 can receive the sample 116 and analyze a headspace of the sample 116. Detection component 120 can analyze the chemical composition of the headspace or analyze a visual aspect of the headspace.

In one implementation, detection component 120 includes a sensory array. The sensory array can comprise an array of polymer films, each polymer film of the array of polymer films can be of a slightly different type. However, it is to be appreciated that various polymer films of the array of polymer films may be of a same type. The electrical conductivity of the different types of films varies in the presence of different chemicals, so that when the array of films is exposed to a particular odor, the different films respond in a characteristic way.

In another example, the sensory array can comprise an array of transistors made out of various semiconductor materials (e.g., silicon oxide sensor). Transistors made of different materials can respond differently to different chemicals, so that the array produces a distinctive signal when exposed to an odor.

In another implementation, the detection component 120 can include visual detectors (e.g., a photoelectric detector). Visual detectors can comprise a light source and a light sensor. The light source produces a light that is aimed at the light sensor. The light sensor can determine when the light is blocked. It is to be appreciated that the detection component can comprise one or more sensors. Further, the sensors can comprise various sensors such as ionization sensors.

Detection component 120 converts the reactions of the sensory array or the visual system into a digital signal. The digital signal represents a chemical composition of the headspace. The memory 140 can store the digital signal. The detection component 120 can compare the digital signal to various other digital signals stored in memory 140 to determine an identity of a source associated with the headspace. In one implementation, detection component 120 uses at least one of a hash table, fuzzy logic, artificial neural network (ANN), or pattern recognition modules, for example, to determine an identity of a source associated with the headspace.

Figure 2:
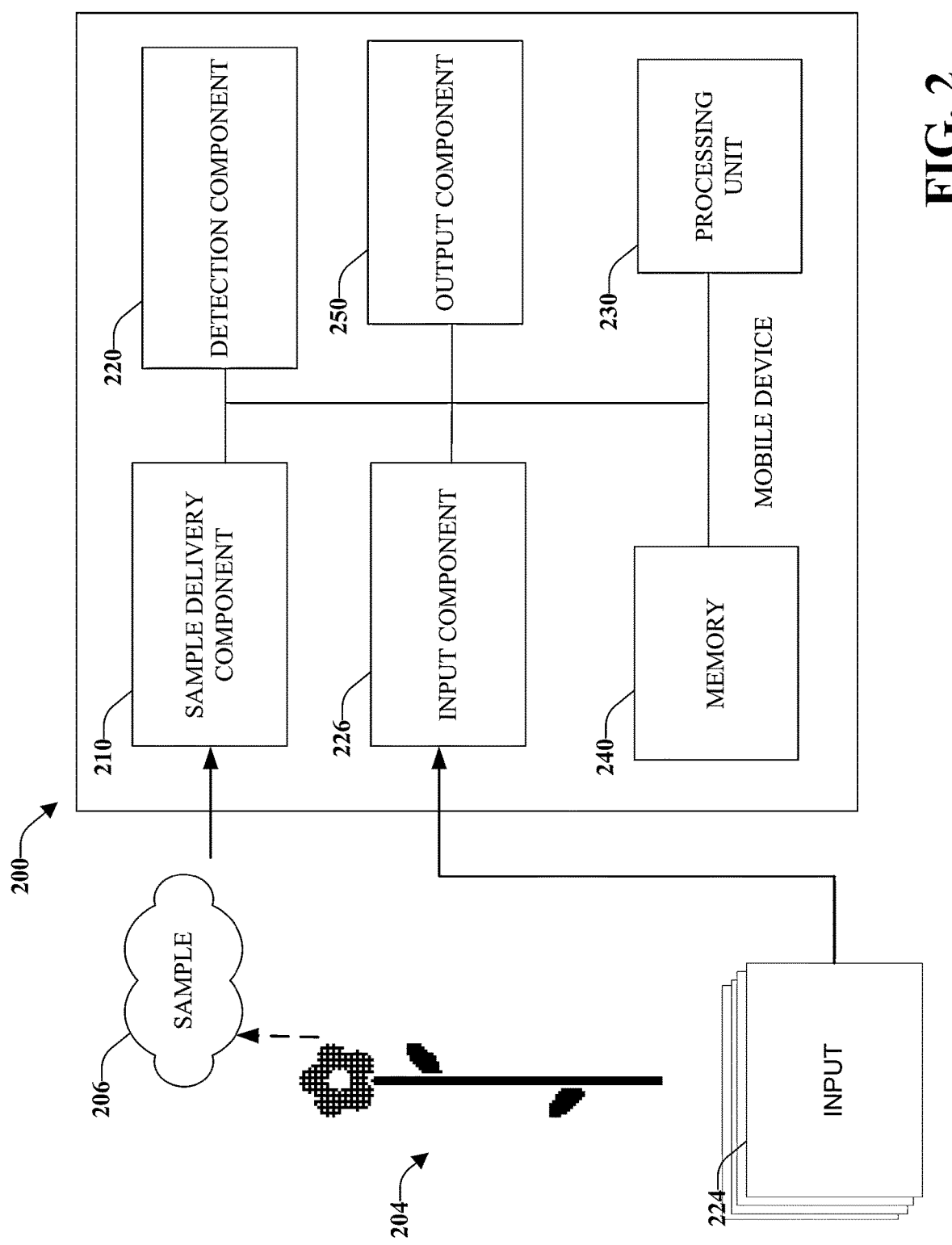
FIG. 2 illustrates a high-level functional block diagram of an example mobile electronic nose device including an input component and an output component.

Now turning to FIG. 2, there illustrated is a non-limiting exemplary embodiment of a mobile device 200 capable of using input 224 to aid in detecting and/or identifying various odors, chemical compounds, aromas, and or gaseous substances. Mobile device 200 comprises a sample delivery component 211, a detection component 220, an input component 226, a computer processing unit (CPU) 230, an output component 250 and a memory 240. Mobile device 200 provides for receiving a sample 206 and detecting or identifying a source 204 associated with sample 206. In one aspect, sample 206 is a portion of air in the proximity of mobile device 200. In another aspect, sample 206 can contain a scent, an odor, chemical(s), airborne particles, or gaseous substance(s).

In one aspect, CPU 230 is capable of executing various components and/or portions of components stored in a computer readable memory 240. Memory 240 can also store a plurality of entries, each entry comprising a digital odor signals, class, and source name, for example. Each entry can also comprise various other fields such as photo identification, date detected, and location, to name a few.

Sample deliver component 211 can actively or passively receive sample 206. Detection component 220 can receive a headspace of sample 206 and analyze the headspace. Detection component 220 can determine a digital odor signal associated with the headspace.

Input component 226 can receive and analyze input 224. Input component 226 can receive input 224 as audio, visual, text and/or other user input. In one aspect, input component 226 includes one or more input interfaces such as a microphone, a camera, a key board, an actuator, a touch screen and/or other user interfaces capable of receiving input 224, for example. In one aspect, input component 226 can receive input 224 relating to source 204 and/or sample 206. For example, input 224 can contain information relating to a source's class, image, and/or location.

In one implementation, input component 226 comprises a microphone. Input component 226 receives input 224 as audio information via the microphone. Input component 226 can identify speech in input 224. Memory 240 can store the digital signal. For example, a user can say "identify this flower" and input component 226 can receive the audio as input 224. In one example, input component 226 can convert the audio to a digital signal and analyze the digital signal.

In another embodiment, input component 226 includes a user interface device, such as a touch screen or keyboard, for example. In one aspect, the user input device can receive input 224 as text. In another implementation, input 224 contains information relating to sample 206 and/or source 204.

As another example, input component 226 can include a camera. The camera can capture visual information. The visual information can be received by input component 226 as input 224. In one aspect, the visual information is an image of source 204. Input component 226 can identification the image as relating to a class of objects, being a specific object, and the like. In one implementation, input component 226 determines if the image of source 204 is associated with an image stored in memory 240. For example, an image is captured and input component 226 determines if the image is an image of a flower.

Detection component 220 receives analyzed input by input component 206. The analyzed input can contain information relating to source 204 and/or sample 206. Detection component 220 applies the analyzed input to narrow and/or improve identification of source 204 associated with sample 206. For example, detection component 220 receives analyzed input containing information such as "flower" and then detection component 220 can compare the analyzed headspace to entries in memory 204 which have a class type of "flower". Detection component 220 can limit its comparison of the digital headspace signal to entries in memory with a class association of "flower".

In another aspect, detection component 220 can receive input 224 or analyzed input from input component 206 which contains a plurality of information relating to a source 204 and/or sample 206. For example, input 224 can contain a date field, a location field and an image field. In one aspect, input 224 can contain a date field and location field. Entries in memory 240 can have associated date ranges and location ranges. Detection component 220 can apply the input 224 to limit searchable entries. For example, a flower may be indigenous to a certain location and may only bloom during a certain date range. Detection component 220 can apply input 224 to reduce the number of possible entries.

Figure 3:
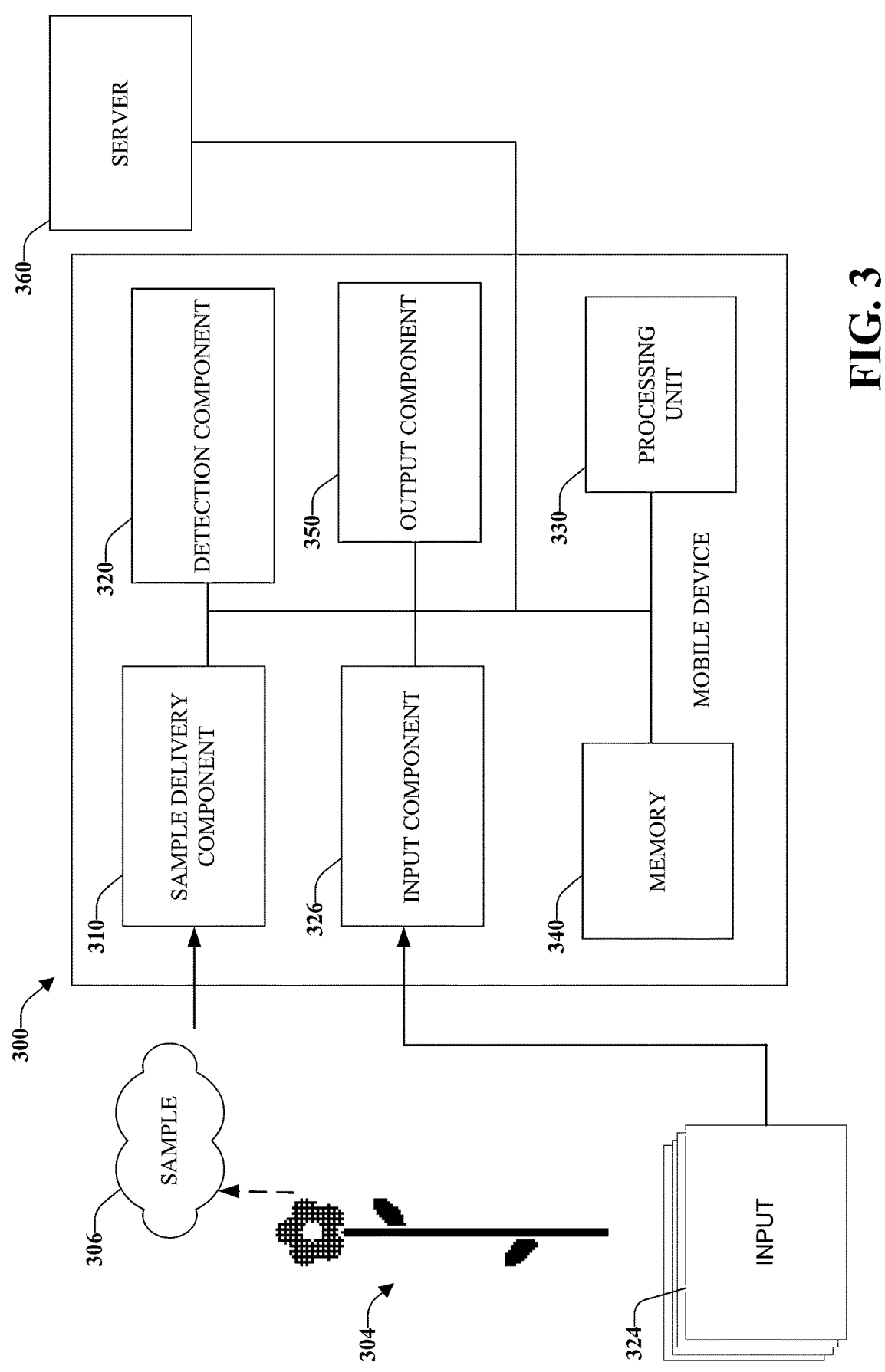
FIG. 3 illustrates a high-level functional block diagram of an example mobile electronic nose device in communication with a server.

Referring now to FIG. 3, there illustrated is a non limiting exemplary embodiment of a mobile device 300 in accordance with various aspects of this disclosure. Mobile device 300 comprises sample delivery component 311, detection component 320, input component 326, processing unit 330, memory 340, and output component 350.

Mobile device 300 can receive a sample 306 associated with a source 304 via a sample delivery component 311. Input component 326 can receive and analyze input 324 containing information relating to sample 306 and/or source 304. Detection component 320 can receive analyzed input and a headspace of sample 306. Detection component 320 can analyze the headspace in conjunction with the analyzed input.

In one aspect, processing unit 330 is capable of executing various components and/or portions of components stored in a computer readable memory 340. Memory 340 can also store a plurality of entries, each entry comprising a digital odor signals, class, and source name, for example. Each entry can also comprise various other fields such as photo identification, date detected, and location, to name a few.

In another aspect, mobile device 300 is in communication with one more server(s) 360. Communications can be facilitated via a wired (including optical fiber) and/or wireless technology. Server(s) 360 comprise one or more server data store(s) that can be employed to store information local to server(s) 360. In one implementation, server(s)'s 360 data store(s) contains one or more entries, each entry relates to unique sources with associated information, such as class, source name, digital identification, and image, for example.

In one implementation, detection component 320 receives entries and/or information relating to entries from server(s) 360. In another aspect, detection component 320 searches entries in server(s)'s 360 data store.

In another implementation, detection component 320 can send information relating to source 304 and or sample 306 to server(s) 360. Server(s) 360 can record information in the server data stores.

Output component 350 can output information. In one embodiment, output component 350 includes one or more output devices such as a speaker, and/or display. Output component 350 outputs information relating to sample 306, source 304 and a detection result. A detection result can include information relating to source 304 such as a determined identity and/or class.

Figure 4:
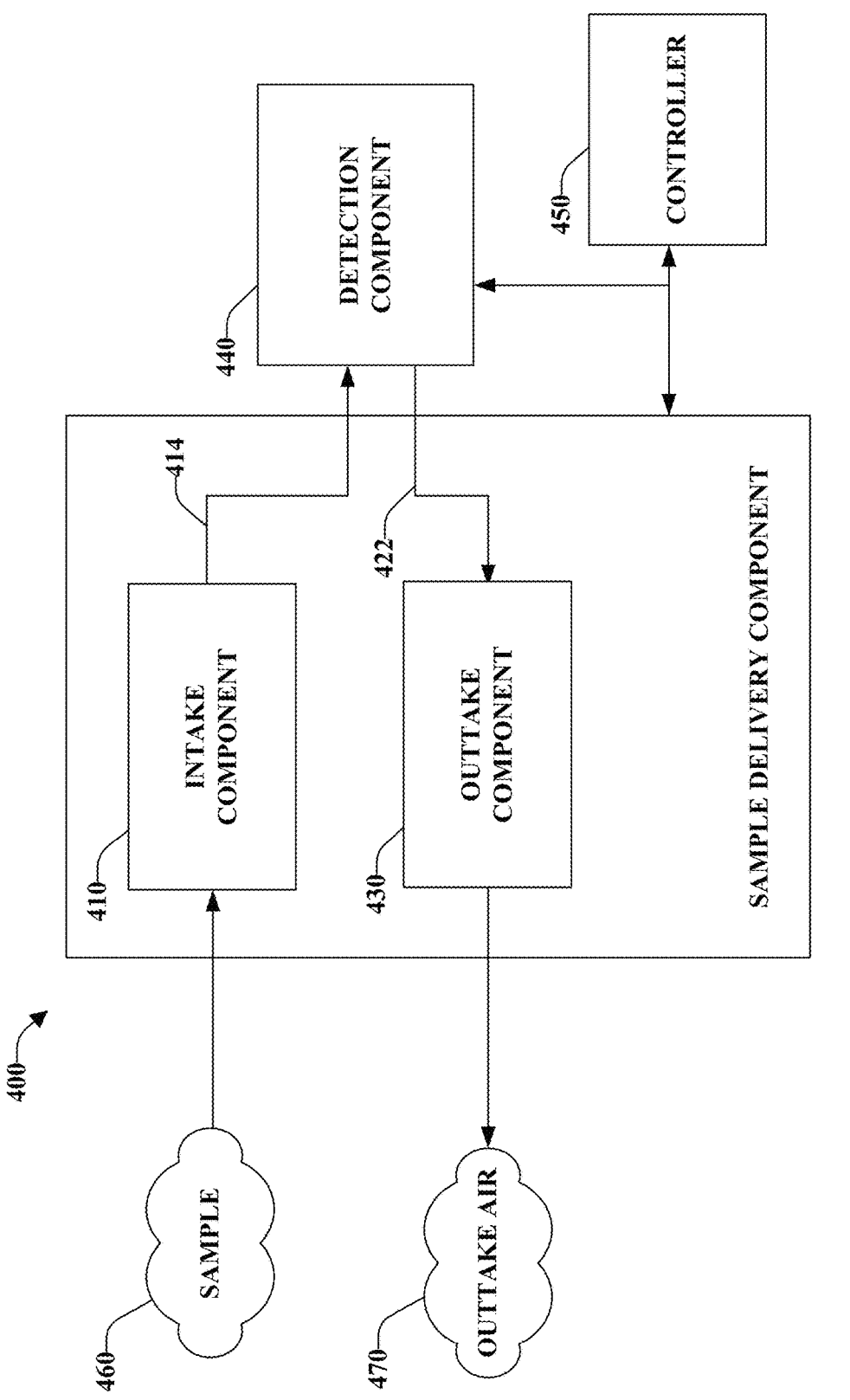
FIG. 4 illustrates a high-level functional block diagram of an example sample delivery component.

Referring now to FIG. 4, there illustrated is sample deliver component 400 which gathers a sample, delivers a sample, and/or removes a sample from a device in accordance with various aspects of this disclosure. Sample delivery component 400 can include am intake component 411, an intake line 414, an outtake line 422, an outtake component 430. A controller 450 can facilitate operation of sample delivery component 400 and various other components in accordance with this disclosure, such as detection component 440.

Intake component 440 gathers or receives a sample 460. In one aspect, intake component 440 passively receives sample 460 as sample 460 diffuses through airspace. In another aspect, input component 440 includes a mechanical device which can draw in sample 460. The mechanical device can include a bladed fan, a bladeless fan or other known devices capable of drawing in air as known in the field.

In another aspect, intake component 411 can comprise one or more apertures in a mobile device. Sample 460 can enter the mobile device through the one or more apertures.

Intake line 414 can transfer or provide a passage to various components in accordance with this disclosure, such as detection component 440, for example. Intake line 414 can be in fluid communication with detection component 440, for example. Intake line 414 can comprise tubing, or other device of plastic, rubber, metal, or other suitable means as known in the art. Detection component 440 can analyze sample 460 or a headspace of sample 460.

Outtake line 422 can fluidly connect various components, such as detection component 440, to outtake component 430. Outtake Air 470 can pass through outtake line 422 and exit the mobile device through outtake component 430. Outtake component 430 can comprise one or more apertures to allow the spent sample 460 or other outtake air 470 to exit the mobile device.

In one aspect, outtake line 422 can comprise tubing, or other device of plastic, rubber, polymer, ceramic, metal, or other suitable means as known in the art.

In one implementation outtake component 430 can comprise a mechanical device for drawing a sample. The mechanical device can include a bladed fan, a bladeless fan or other known devices (e.g., micro electro mechanical systems (MEMS) devices) capable of drawing in air as known in the field. For example, a system containing sensors and microjet MEMS actuators can be employed to exact some flow control, and synthetic jets can be employed to reduce drag and modify flow over air foils and bluff bodies. In one aspect, outtake component 430 and intake component 411 can each comprise one or more mechanical device. In another implementation, intake component 411 or outtake component 430 can utilize the same one or more mechanical devices. In another aspect, outtake component 430 can include a mechanical device that causes air to pass through input component 411 and output component 430.

In another implementation, outtake component 430 and intake component 411 can both utilize the same one or more apertures to allow air to enter and exit a mobile device.

Figure 5:
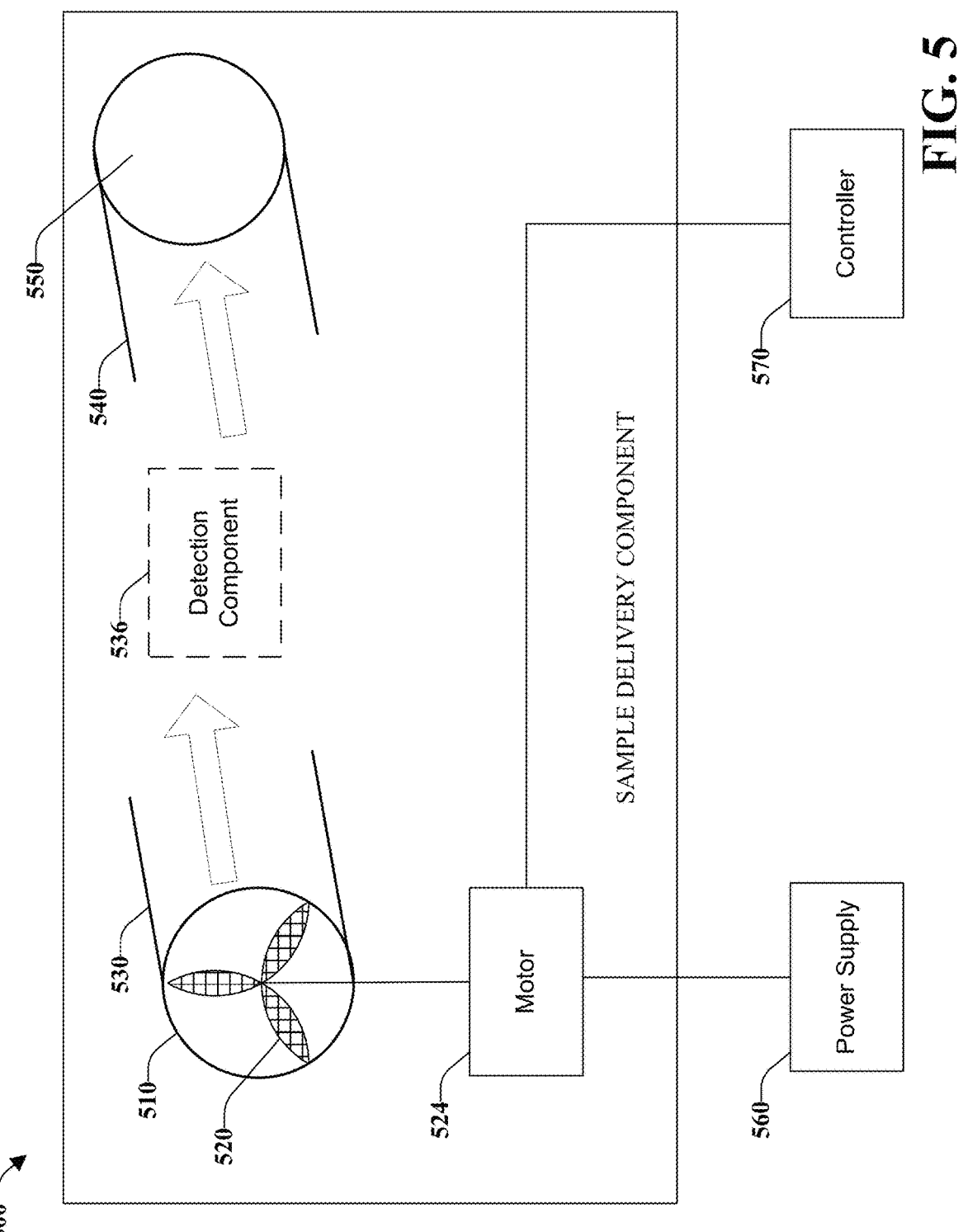
FIG. 5 illustrates an example schematic diagram of a sample delivery component.

Referring now to FIG. 5, there illustrated is a schematic diagram of an exemplary sample delivery component 500 in accordance with various aspects of this disclosure. In accordance with various aspects of this disclosure, sample delivery component 500 can gather a sample in air space, deliver the sample to various components in a mobile device, and remove the gathered sample from the mobile device.

Sample delivery component 500 can comprise one or more intake apertures 511, fan 520, motor 524, intake duct 530, outtake duct 540, and one or more outtake apertures 550. A controller 570 can control various aspects of sample delivery component 500. Further, a power supply 560 can power various aspects of sample delivery component 500 such as fan 524, for example.

A sample can be received through one or more intake apertures 511. Fan 520 can draw in the sample. Likewise, motor 524 can receive power from power supply 560. As fan 520 rotates, it creates a low pressure area in the mobile device with respect to the airspace outside the device. Air is then caused to enter the one or more intake apertures 511.

The sample can pass through intake duct 530. Intake duct 530 can be in communication with various components, such as detection component 536. The sample can also pass through or be forces through outtake duct 540. The spent sample can then exit through one or more outtake apertures 550.

In other implementation, the intake duct 530 and outtake duct 540 can be of one unitary construction or modular construction. Likewise, power supply 560 can be a battery, fuel cell or other power source. Power supply 560 can be within sample delivery component 500 or can be a power supply for a larger mobile device. In another aspect, the one or more intake apertures 511 and one or more outtake apertures 550 can comprise the same one or more outtake apertures.

Figure 6:
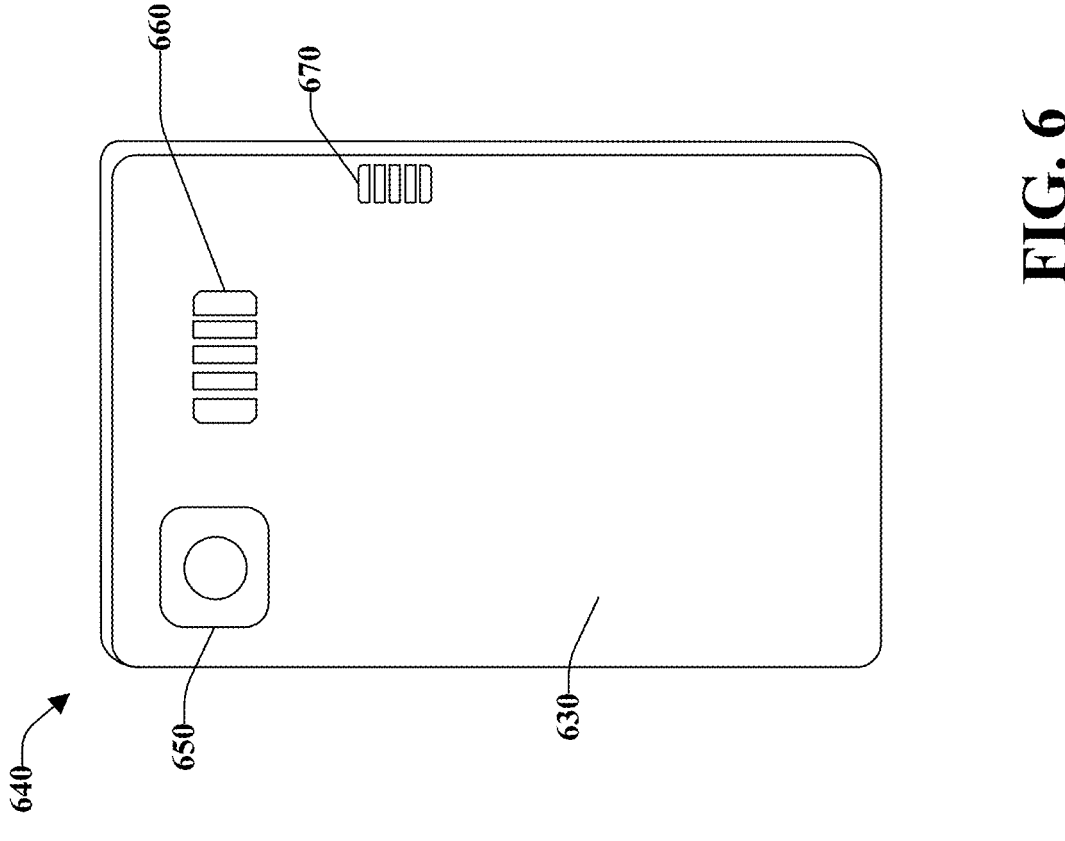
FIG. 6 illustrates a schematic diagram of an external view of example mobile electronic nose device.
Figure 6:
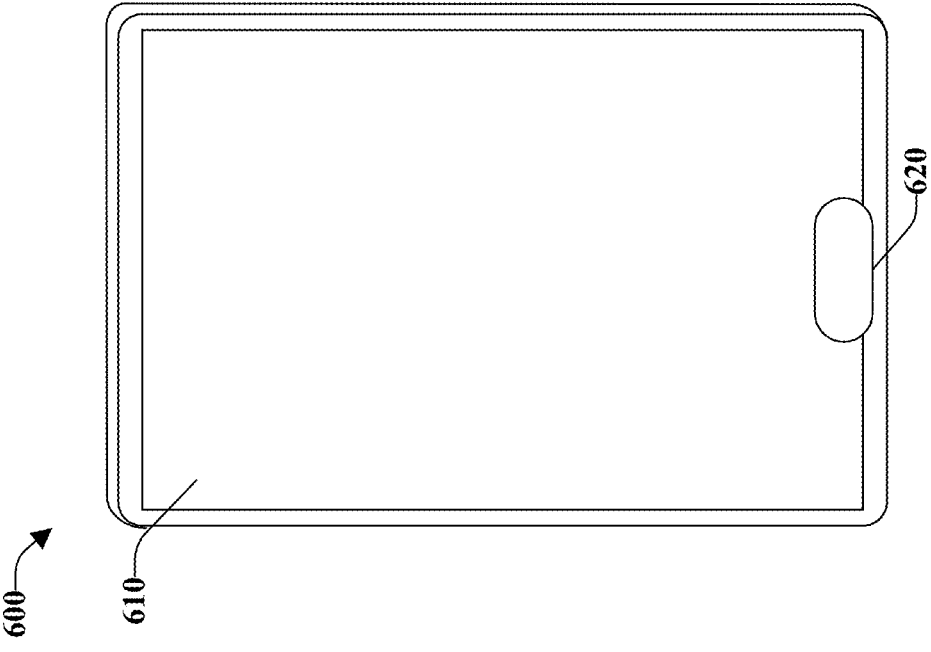

Turning now to FIG. 6, there illustrated is an exemplary schematic diagram of a mobile device in accordance with this disclosure, as seen from a front view 600 and a back view 640. The mobile device includes a display 611, a microphone 620, a housing 630, a camera 650, a first at least one opening 660 and a second at least one opening 670.

Housing 630 comprises a shell or enclosure that houses various components in accordance with the claimed subject matter. Housing 630 can be made of a unitary or multi-piece construction and can consist of one or more of metal, glass, plastic, ceramic, polymer, wood, and other material known in the art.

In one aspect, display 611 can be a touch screen, monitor, digital display, and or other screen as known in the art. Display 611 can receive input from a user in accordance with various aspects of this specification. For example, display 611 can receive input regarding a sample of an odor, airborne gas or chemical and can receive commands through user interaction.

In one implementation, microphone 620 can receive user input. For example, microphone 620 receives audio from a user such as "identify this flower". Various components in this disclosure can receive captured input, for example, an identification component can receive a captured image.

In another aspect, camera 650 can receive and or capture visual input. For example, camera 650 can be pointed at a source object. Camera 650 can capture an image or images of the source object. Various components in this disclosure can receive captured input, for example, an identification component can receive a audio input In another aspect, the first at least one opening 660 can serve as an opening for a speaker, a heat ventilation and/or an intake for a sample delivery component in accordance with various aspects of this disclosure. In one implementation, the first at least one opening 660 comprises a plurality of slits, openings, or apertures in housing 630.

Similarly, the second at least one opening 670 can serve as an opening for a speaker, a heat ventilation and/or an outtake for a sample delivery component in accordance with various aspects of this disclosure. In one implementation, second at least one opening 670 comprises a plurality of slits, openings, or apertures in housing 630.

In another implementation, the first at least one opening 660 and the second at least one opening 670 can comprise the same at least one openings. Thus, the amount of openings can be reduced.

Figure 7:
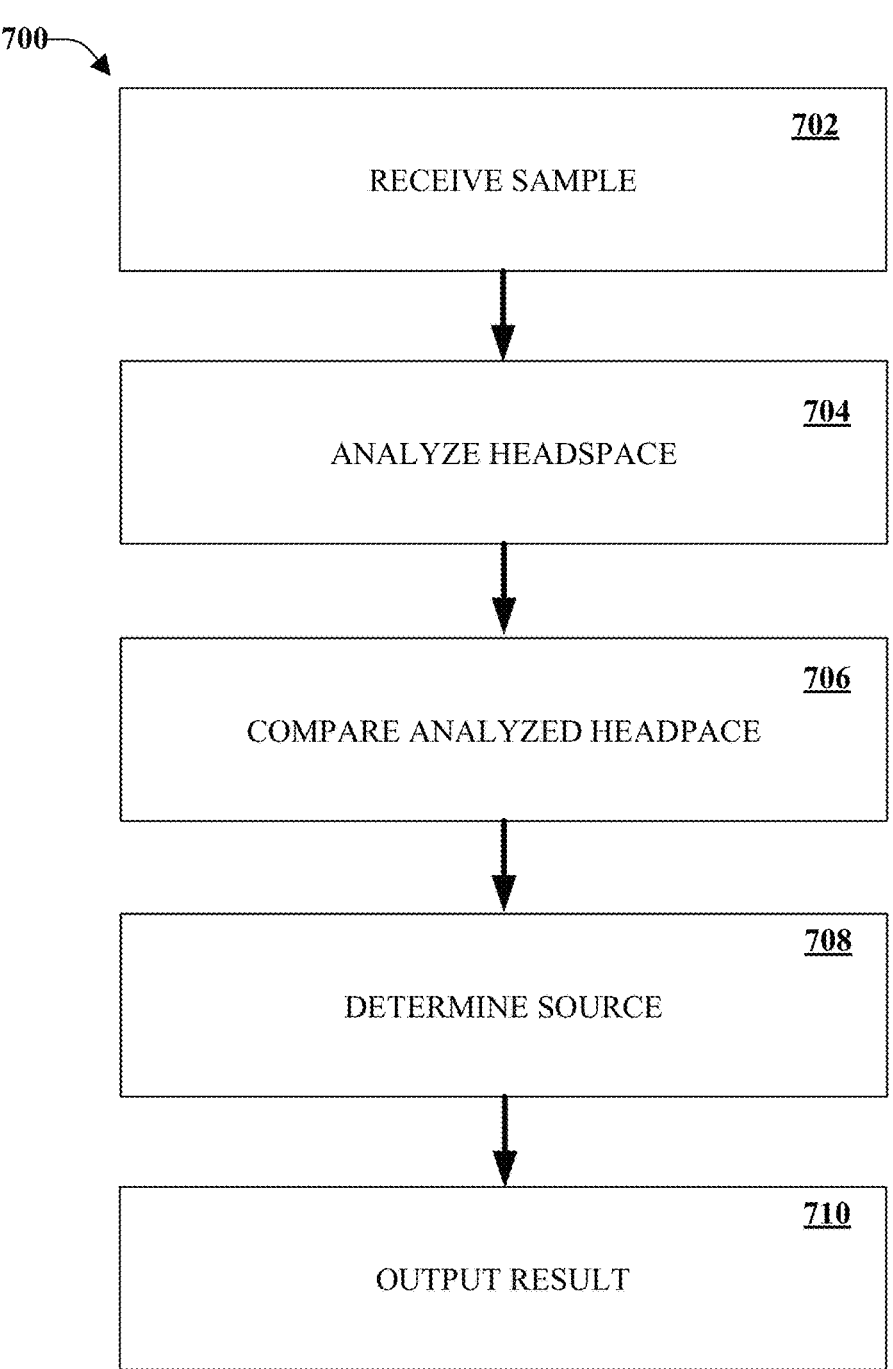
FIG. 7 illustrates an example methodology for gathering and analyzing a sample.
Figure 8:
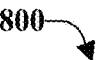
FIG. 8 illustrates an example methodology for gathering and analyzing a sample including receiving input and analyzing a sample with the received input.
Figure 8:
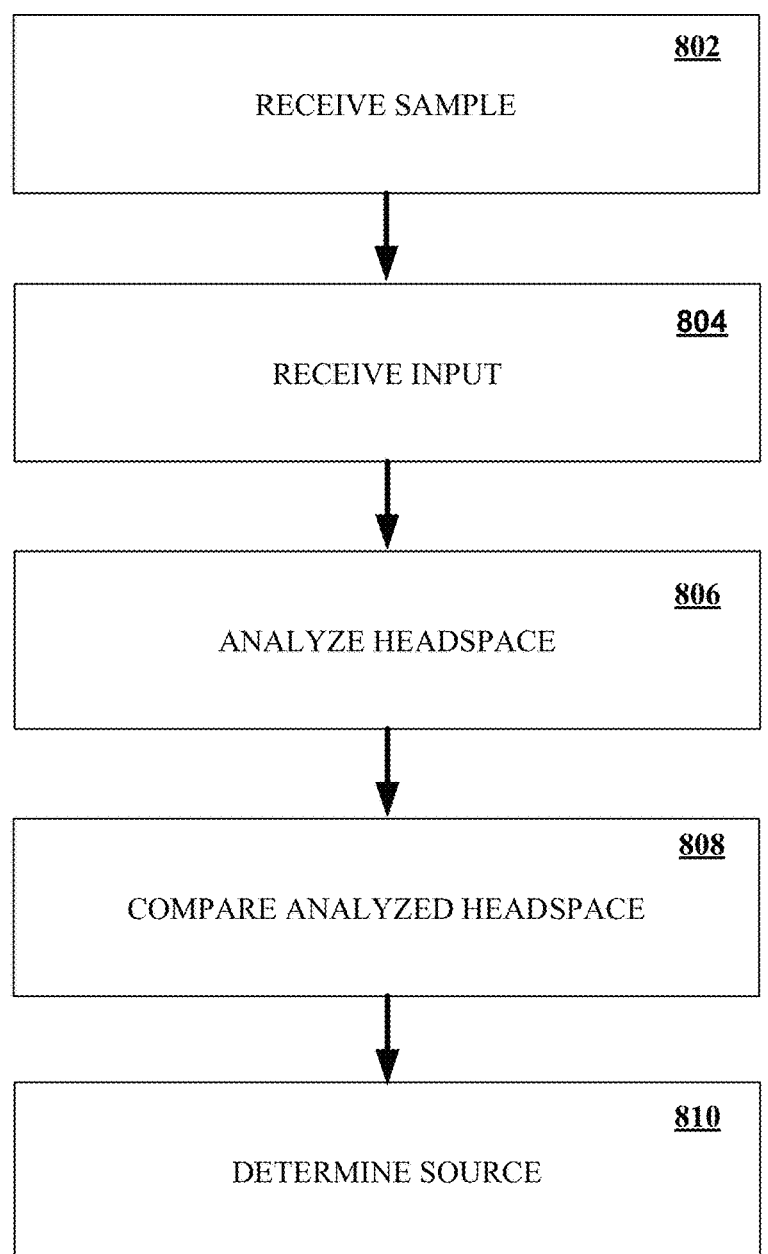
Figure 9:
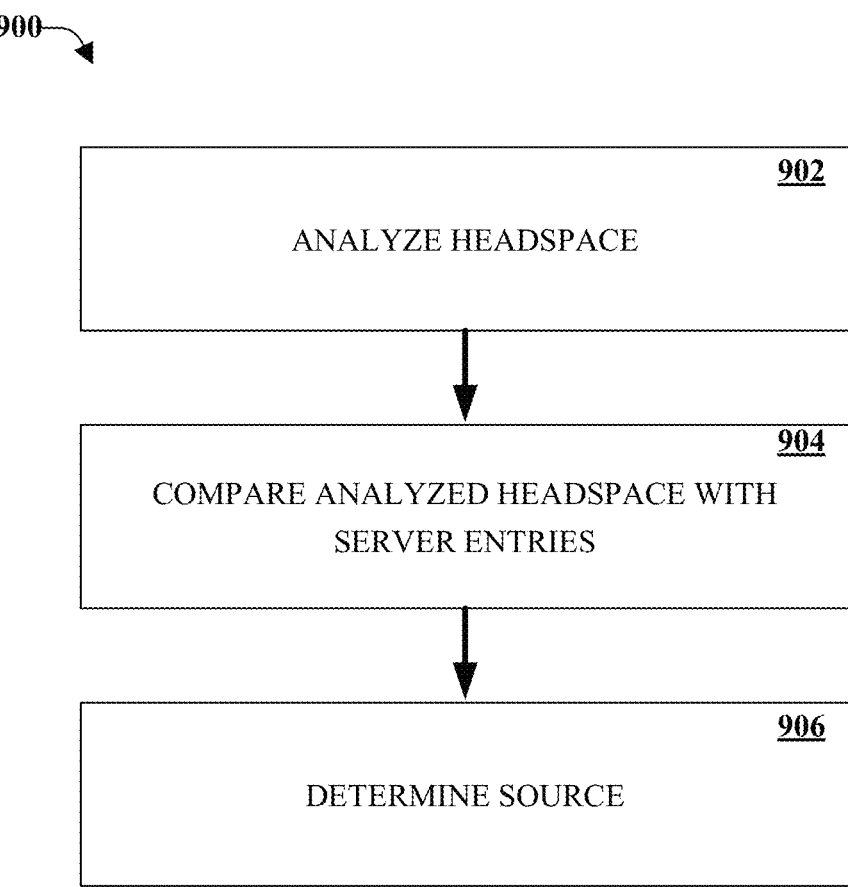
FIG. 9 illustrates an example methodology for determining a source of a sample including connecting to a server.

Referring now to FIGS. 7-9, there are illustrated methodologies and/or flow diagrams in accordance with the disclosed subject matter. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer readable device or storage medium.

With reference to FIG. 7, there is illustrated a methodology 700 for determining and/or identifying a source of a sample in accordance with various aspects of this disclosure. As an example, various media applications, such as, but not limited to, mobile devices such as smart phones, tablets, PDA's, cooking utensils, and cookware can use methodology 700. Specifically, methodology 700 receives a sample and identifies the sample as associated with a source.

A mobile device can receive a sample via a sample delivery component at 702, (e.g., sample delivery component 111). For example, a fan can cause a sample to enter at least one aperture in a housing of a mobile device. In another example, a sample can passively enter at least one aperture in a housing of a mobile device at 702. As such, a mobile device can continuously monitor an airspace, such as to detect smoke or various chemical compounds in an airspace.

At 704, a headspace of the sample can be analyzed by a detection component, for example. Analysis of a headspace can include a visual analysis and/or a chemical analysis (e.g., via a sensory array).

At 706, an analyzed headspace can be compared with entries in a memory, such as memory 114. Comparison can comprise comparing substances and/or compounds in the analyzed headspace with substances and/or compounds associated with entries in a memory.

At 708, the source associated with the headspace can be identified via a detection component, such as detection component 120. The analyzed and compared headspace can be associated with a best matched entry or set of entries. For example, a hash table analysis can result in one or more entries being associated with the headspace.

At 711, the identified source can be output as a result via an output component, such as output component 250. The output result can include a name of a source or sources, images of a source or sources, and/or additional associated information. The additional associated information can include genes, definition, common location, and the like.

Turning now to FIG. 8, there is illustrated a methodology 800 for determining and/or identifying a source of a sample in accordance with various aspects of this disclosure. As an example, various media applications, such as, but not limited to, mobile devices such as smart phones, tablets, PDA's, cooking utensils, and cookware can use methodology 800. Specifically, methodology 800 receives a sample and identifies the sample as associated with a source with use of additional input.

At 802, a sample is received via a sample delivery component (e.g., sample delivery component 111). For example, a fan can cause a sample to enter at least one aperture in a housing of a mobile device. In another example, a sample can passively enter at least one aperture in a housing of a mobile device at 802. As such, a mobile device can continuously monitor an airspace, such as to detect smoke or various chemical compounds in an airspace.

At 804, input is received and/or captured via one or more input component(s), such as display 611, a microphone 620, a housing 630, and/or a camera 650. Input can comprise multiple inputs such as but not limited to user input, captured image, location information, date information, and captured audio.

At 806, a headspace of the sample and input are analyzed by a detection component, such as detection component 120, for example. In one aspect, analysis of a headspace can include a visual analysis and/or a chemical analysis (e.g., via a sensory array). In another aspect, analysis of input can include audio analysis, text analysis, image analysis, location and date analysis, for example.

At 808, the analyzed headspace and the analyzed input are compared with entries in a memory, such as memory 114, for example. Comparison can include reducing possible sources to a set of possible sources via analyzed input, such as through a hash table, fuzzy logic and the like, via components executed by a CPU, such as CPU 130. In another aspect, the analyzed headspace can be compared to the reduced set of possible sources.

At 811 a source or set of sources of the sample is determined, via a detection component, for example. In one aspect, the source or set of sources can be associated with the analyzed sample and the analyzed input. The association can be stored in memory, such as memory 114, for example.

Turning now to FIG. 9, there is illustrated a methodology 900 for determining and/or identifying a source of a sample in accordance with various aspects of this disclosure. As an example, various media applications, such as, but not limited to, mobile devices such as smart phones, tablets, PDA's, cooking utensils, and cookware can use methodology 900. Specifically, methodology 900 receives a sample and identifies the sample as associated with an entry in a data store.

At 902, a headspace of a received sample is analyzed, (e.g. by detection component 111). Analysis of a headspace can include a visual analysis and/or a chemical analysis (e.g., via a sensory array).

At 904, can analyzed headspace can be compared with entries in a server, such as server 360. In one aspect, the server can comprise a memory. The memory can contain a set of entries. Each entry of the set of entries can comprise a number of fields, such as a source name, source id, date range, location, genera, genus, class, image and the like.

At 906, a source can be determined as associated with the analyzed headspace. In one aspect, a set of source can be determined as possible sources associated with the analyzed headspace.

The systems and processes described below can be implemented within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders that are not all of which may be explicitly illustrated herein.

Figure 10:
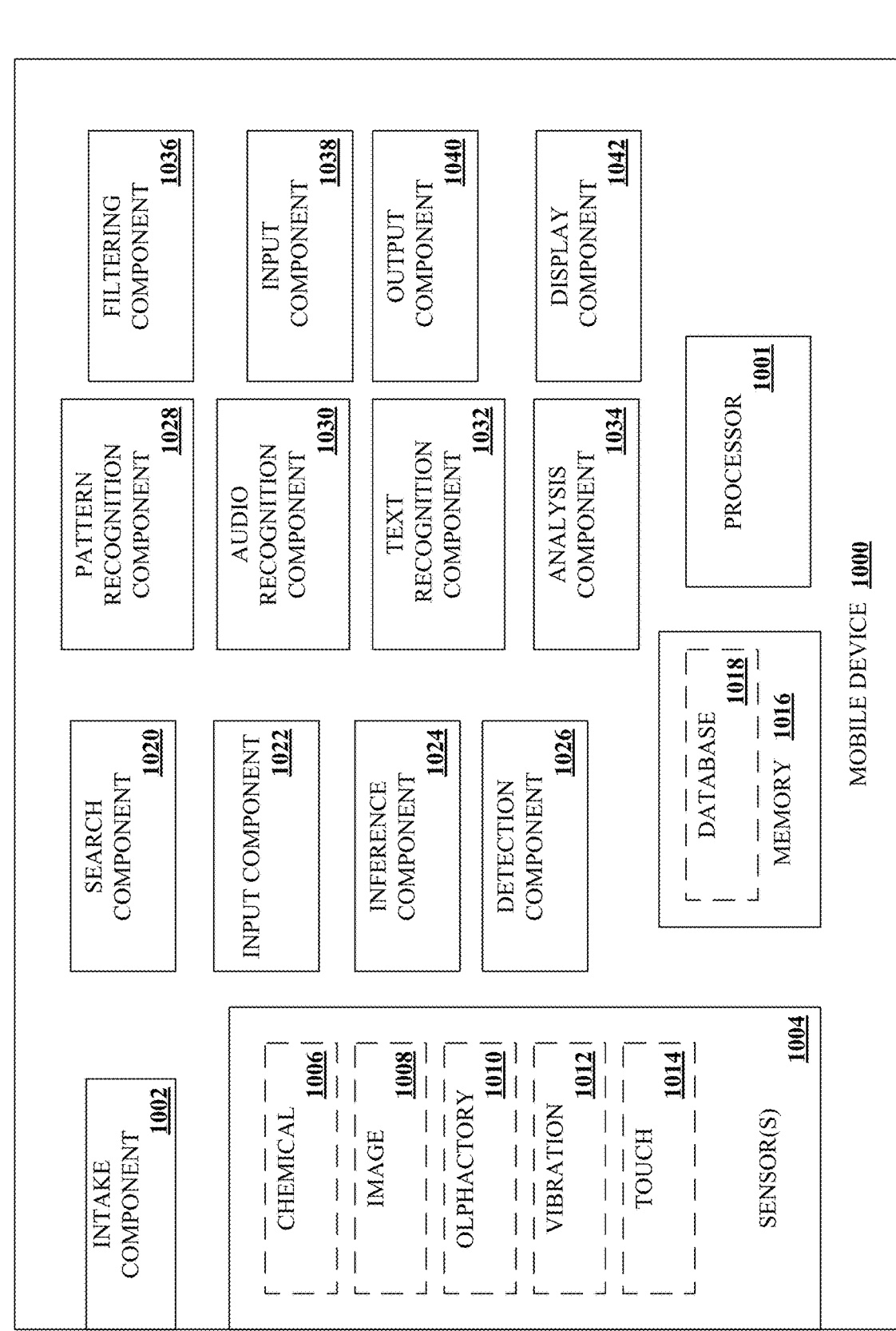
FIG. 10 illustrates a high-level functional block diagram of an example mobile electronic nose device.

FIG. 10 illustrates an embodiment of a mobile device 1000 (e.g., personal digital assistants (PDAs), audio/video devices, mobile phones, MPEG-1 Audio Layer 3 (MP3) players, personal computers, laptops, tablets, etc.) that includes various optional components in connection with functionalities disclosed herein. The mobile device 1000 includes a processor 1001 and memory 1016. The components can be electrically and/or communicatively coupled to one another to perform various functions. An intake component 1002 collects a sample (e.g., air, gas, vapor, . . . ) in connection with electronic olfactory-based identification thereof. The intake component can passively collect samples or actively (e.g., employment of a fan, suction, MEMs device, negative pressure, or any other suitable means for collection a sample). A set of sensors 1004 sense properties associated with the sample or inputs to the device 1000. The sensors 1004 can optionally include any one or more of the following: chemical sensor 1006, image sensor 1008, olfactory sensor 1011, vibration sensor 1012, or touch sensor 1014. It is to be appreciated that other suitable sensors can be employed in connection with device 1000.

Search component 1020 can be employed to allow a user to search for information, e.g., via the Internet, to augment identification of a sample. In an aspect, the search results can be ordered as a function of relevancy to the search criteria, relevancy to user preferences, or rankings associated with the search results. The search component 1020 can be implemented on a manual basis (e.g., user input), or in an automated manner. For example, the search component 1020 can regularly or constantly run searches (e.g., in the background to generate content that is relevant to a user at a current point in time).

An input component 1022 can receive information about a source (e.g., of a smell). A detection component 1026 can detect presence and amount of chemicals in the headspace, e.g., collected by the sensors 1004. The sensors 1004 can react to various chemicals within a headspace. The reaction can cause a change in physical or electrical properties of respective sensors. In one example, absorption of the chemicals in the headspace causes physical alterations of various sensors in the set of sensors. Each sensor can react differently to the various chemicals. The processor 1001 can transform the reactions of the sensory array into a digital signal. For example, the digital signal can be computed based on a statistical model. In one non-limiting embodiment, an organic ultra-thin transistor chemical sensor having a channel that consists of one or a few monolayers can be employed. The organic thin film transistor chemical sensors can have nearly monolayer thin film channels that act as highly-sensitive detectors of trace levels of organic vapors and can perform quantitative vapor analysis. The organic ultra-thin film can be permeable to a chemical analyte of interest.

An inference component 1024 can infer actions or conclusions in connection with identification of a source or compound associated with a gather sample. As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. The inference component can perform a utility-based analysis in connection with making an inference. For example, the cost of making an incorrect inference can be weighed against the benefit of making a correct inference.

Detection component 1026 can analyze chemical composition of a sample or analyze a visual aspect of the sample. Pattern recognition component 1028 can identify images captured by the device (e.g., via a camera component). Audio recognition component 1030 can identify sources of audio received by the device. The device also includes a text recognition component 1032. An analysis component 1034 analyzes information received from other components and can perform an analysis in connection with identifying source, smell, attribute, feature, composition, or the like associated with a sample.

Filtering component 1036 can employ and filter information to facilitate quickly converging on identification of source, smell, attribute, feature, composition, or the like in connection with a sample. For example, null items or features can be ruled out as potential candidates in connection with determining identification. Input component 1038 receives input, e.g., from a user. The input component 1038 can receive for example, text, typed input, verbal or audio input, image input, gesture input, or any suitable type of input for inputting information. Output component 1040 outputs results of the analyses performed herein. Display component 1042 displays results of the analyses.

Figure 11:
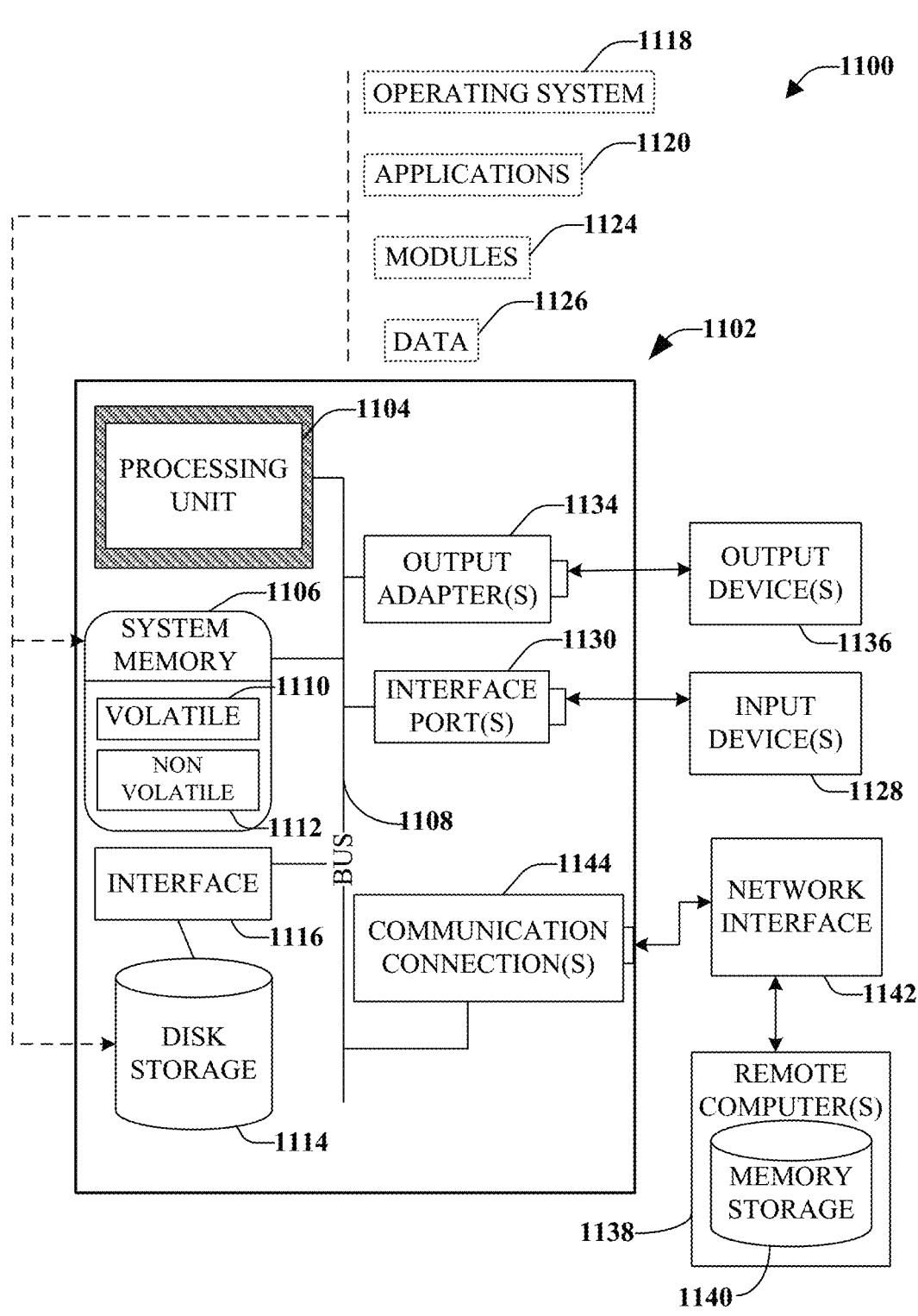
FIG. 11 illustrates an example schematic block diagram of a computing environment in accordance with this specification.

With reference to FIG. 11, a suitable environment 1100 for implementing various aspects of the claimed subject matter includes a computer 1102. The computer 1102 includes a processing unit 1104, a system memory 1106, a codec 1105, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1106 includes volatile memory 1111 and non-volatile memory 1112. The basic input/output system (BIOS), containing the basic routines to transfer information between elements within the computer 1102, such as during start-up, is stored in non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), or flash memory. Volatile memory 1111 includes random access memory (RAM), which acts as external cache memory. According to present aspects, the volatile memory may store the write operation retry logic (not shown in FIG. 11) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM).

Computer 1102 may also include removable/non-removable, volatile/non-volatile computer storage media. FIG. 11 illustrates, for example, a disk storage 1114. Disk storage 1114 includes, but is not limited to, devices like a magnetic disk drive, solid state disk (SSD) floppy disk drive, tape drive, Zip drive, LS-110 drive, flash memory card, or memory stick. In addition, disk storage 1114 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1114 to the system bus 1108, a removable or non-removable interface is typically used, such as interface 1116.

It is to be appreciated that FIG. 11 describes software, software in execution, hardware, and/or software in combination with hardware that acts as an intermediary between users and the basic computer resources described in the suitable operating environment 1100. Such software includes an operating system 1118. Operating system 1118, which can be stored on disk storage 1114, acts to control and allocate resources of the computer system 1102. Applications 1120 take advantage of the management of resources by operating system 1118 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems. For example, applications 1120 and program data 1126 can include software implementing aspects of this disclosure.

A user enters commands or information into the computer 1102 through input device(s) 1128, non-limiting examples of which can include a pointing device such as a mouse, trackball, stylus, touch pad, keyboard, microphone, joystick, game pad, satellite dish, scanner, TV tuner card, digital camera, digital video camera, electronic nose, web camera, and any other device that allows the user to interact with computer 11311. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s) 1128. Thus, for example, a USB port may be used to provide input to computer 1102, and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices and/or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire and/or wireless communication networks such as local-area networks (LAN), wide-area networks (WAN), and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, wired and wireless Ethernet cards, hubs, and routers.

Figure 12:
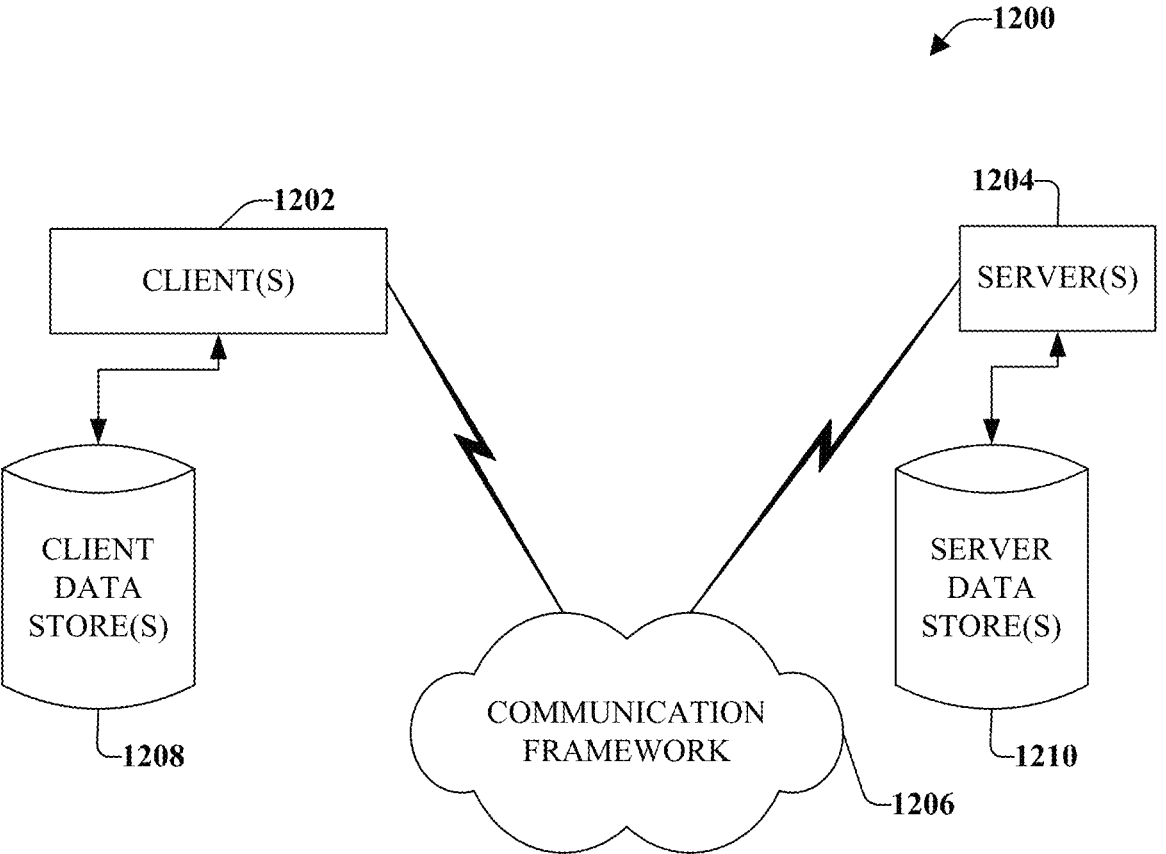
FIG. 12 illustrates an example block diagram of a computer operable to execute various implementations described herein.

Referring now to FIG. 12, there is illustrated a schematic block diagram of a computing environment 1200 in accordance with this specification. The system 1200 includes one or more client(s) 1202, (e.g., computers, smart phones, tablets, cameras, PDA's). The client(s) 1202 can be hardware and/or software (e.g., threads, processes, computing devices). The client(s) 1202 can house cookie(s) and/or associated contextual information by employing the specification, for example.

The system 1200 also includes one or more server(s) 1204. The server(s) 1204 can also be hardware or hardware in combination with software (e.g., threads, processes, computing devices). The servers 1204 can house threads to perform transformations of media items by employing aspects of this disclosure, for example. One possible communication between a client 1202 and a server 1204 can be in the form of a data packet adapted to be transmitted between two or more computer processes wherein data packets may include coded analyzed headspaces and/or input. The data packet can include a cookie and/or associated contextual information, for example. The system 1200 includes a communication framework 1206 (e.g., a global communication network such as the Internet) that can be employed to facilitate communications between the client(s) 1202 and the server(s) 1204.

Communications can be facilitated via a wired (including optical fiber) and/or wireless technology. The client(s) 1202 are operatively connected to one or more client data store(s) 1208 that can be employed to store information local to the client(s) 1202 (e.g., cookie(s) and/or associated contextual information). Similarly, the server(s) 1204 are operatively connected to one or more server data store(s) 1211 that can be employed to store information local to the servers 1204.

In one exemplary implementation, a client 1202 can transfer an encoded file, (e.g., encoded media item), to server 1204. Server 1204 can store the file, decode the file, or transmit the file to another client 1202. It is to be appreciated, that a client 1202 can also transfer uncompressed file to a server 1204 and server 1204 can compress the file and/or transform the file in accordance with this disclosure. Likewise, server 1204 can encode information and transmit the information via communication framework 1206 to one or more clients 1202.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein (e.g., detection components, input components, sample delivery components, and the like) can include electrical circuit(s) that can include components and circuitry elements of suitable value in order to implement the aspects of this innovation(s). Furthermore, it can be appreciated that many of the various components can be implemented on one or more integrated circuit (IC) chips. In one exemplary implementation, a set of components can be implemented in a single IC chip. In other exemplary implementations, one or more of respective components are fabricated or implemented on separate IC chips.

What has been described above includes examples of the implementations of the present invention. It is, of course, not possible to describe every conceivable combination of components or methodologies for purposes of describing the claimed subject matter, but it is to be appreciated that many further combinations and permutations of this innovation are possible. Accordingly, the claimed subject matter is intended to embrace all such alterations, modifications, and variations that fall within the spirit and scope of the appended claims. Moreover, the above description of illustrated implementations of this disclosure, including what is described in the Abstract, is not intended to be exhaustive or to limit the disclosed implementations to the precise forms disclosed. While specific implementations and examples are described herein for illustrative purposes, various modifications are possible that are considered within the scope of such implementations and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/ circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than or equal to 11" can include any and all sub-ranges between (and including) the minimum value of zero and the maximum value of 11, that is, any and all sub-ranges having a minimum value of equal to or greater than zero and a maximum value of equal to or less than 11, e.g., 1 to 5. In certain cases, the numerical values as stated for the parameter can take on negative values.

In addition, while a particular feature of this innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Reference throughout this specification to "one implementation," or "an implementation," means that a particular feature, structure, or characteristic described in connection with the implementation is included in at least one implementation. Thus, the appearances of the phrase "in one implementation," or "in an implementation," in various places throughout this specification are not necessarily all referring to the same implementation. Furthermore, the particular features, structures, or characteristics may be combined in any suitable manner in one or more implementations.

Further, references throughout this specification to an "item," or "file," means that a particular structure, feature or object described in connection with the implementations are not necessarily referring to the same object. Furthermore, a "file" or "item" can refer to an object of various formats.

As used in this application, the terms "component," "module," "system," or the like are generally intended to refer to a computer-related entity, either hardware (e.g., a circuit), a combination of hardware and software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. While separate components are depicted in various implementations, it is to be appreciated that the components may be represented in one or more common component. Further, design of the various implementations can include different component placements, component selections, etc., to achieve an optimal performance. Further, a "device" can come in the form of specially designed hardware; generalized hardware made specialized by the execution of software thereon that enables the hardware to perform specific function (e.g., media item aggregation); software stored on a computer readable medium; or a combination thereof.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A mobile device comprising:

a processor operatively coupled to an electronic nose, wherein the processor executes computer-executable components stored in memory, the computer-executable components comprising at least:

an image detection component that comprises a camera configured to capture a digital image of a physical source emitting the airborne sample and generate a digital signal representing the image;

an analysis component that processes the digital signal to identify characteristics associated with the physical source;

an input component that accesses stored representations of known sources maintained in memory, each stored representation comprising a digital signal corresponding to a known source, and compares the digital signal and stored representations to determine a degree of correspondence between the digital signal and the stored representations;

an inference component that determines a probability of a match between the analyzed digital signal and at least one stored representation of a known source and outputs an identification of the physical source based on the probability of a match; and a detection component that includes a sensor array of polymer films or transistors configured to detect the airborne sample and output signal data associated with the sample, wherein the detection component further comprises one or more visual detectors.

2. The mobile device of claim 1, wherein the inference component infers actions or conclusions in connection with the identification of the source.

3. The mobile device of claim 1, further comprising:

a filter component that filters information related to the source, received from various sensors employed by the mobile device, to facilitate quick convergence on the identification of the source by ruling out null items as potential candidates.

4. The mobile device of claim 1, wherein the memory includes volatile memory and non-volatile memory.

5. The mobile device of claim 1, further comprising:

A filtering component that employs and filters information to facilitate quickly converging on identification of the source.

6. The mobile device of claim 1, wherein the inference component generates a probability distribution pertaining to potential candidate matches.

7. The mobile device of claim 1, further comprising:

A search component that performs an internet-based search to further facilitate the identification of the source.

8. The mobile device of claim 1, further comprising:

A Global Positioning System (GPS) component that detects a geographical location of the source.

9. The mobile device of claim 1, wherein the detection component converts changes in physical or electrical properties of the sensor array into a digital headspace signature, and the analysis component performs a pattern recognition operation selected from principal component analysis, multiple linear regression, discriminant function analysis, or cluster analysis to assist in identifying the physical source.

10. A method, comprising:

capturing, by a system operatively coupled to a processor, a digital image of a physical source emitting an airborne sample using a camera to generate a digital signal representing the image;

analyzing, by the system, the digital signal to identify characteristics associated with the physical source;

accessing, by the system, stored representations of known sources maintained in memory, each stored representation comprising a digital signal corresponding to a known source;

comparing, by the system, the digital signal and the stored representations to determine a degree of correspondence between the digital signal and the stored representations;

detecting, by the system, the airborne sample using a detection component comprising a sensor array of polymer films or transistors configured to output signal data associated with the airborne sample, the detection component further comprising one or more visual detectors;

determining, by the system, a probability of a match between the analyzed digital signal and at least one stored representation of a known source; and outputting, by the system, an identification of the physical source based on the probability of a match.

11. The method of claim 10, further comprising:

Filtering, by the system, information related to the source.

12. The method of claim 11, wherein the information related to the source is received from various sensors employed by the mobile device.

13. The method of claim 10, further comprising:

Inferring actions or conclusions in connection with the identification of the source.

14. The method of claim 10, further comprising:

Analyzing, by the system, a visual aspect of the sample using a light-based detection sensor configured to output signal data associated with the sample.

15. The method of claim 10, further comprising:

Generating, by the system, a probability distribution pertaining to potential candidate matches.

16. The method of claim 10, wherein the analyses performed by the system includes selecting the best candidate match among images stored in memory.

17. The method of claim 10, further comprising:

Performing, by the system, an internet-based search to further facilitate the identification of the source.

18. A non-transitory computer-readable medium, comprising executable instructions that, when executed by a processor, facilitate performance of operations, comprising:

capturing, by the processor, a digital image of a physical source emitting an airborne sample using a camera to generate a digital signal representing the image;

analyzing, by the processor, the digital signal to identify characteristics associated with the physical source;

accessing, by the processor, stored representations of known sources maintained in memory, each stored representation comprising a digital signal corresponding to a known source;

comparing, by the processor, the digital signal and the stored representations to determine a degree of correspondence between the digital signal and the stored representations;

detecting, by the processor, the airborne sample using a detection component comprising a sensor array of polymer films or transistors configured to output signal data associated with the airborne sample, the detection component further comprising one or more visual detectors;

determining, by the processor, a probability of a match between the analyzed digital signal and at least one stored representation of a known source; and outputting, by the processor, an identification of the physical source based on the probability of a match.

19. The non-transitory computer-readable medium of claim 18, wherein the operations further comprise:

Performing, by the processor, an internet-based search to further facilitate the identification of the source.

20. The non-transitory computer-readable medium of claim 18, wherein the operations further comprise:

Identifying, by the processor, sources of audio, related to the source of the airborne sample, received by a mobile device.

* * * * *